(12) United States Patent
Yanez

(10) Patent No.: US 11,083,926 B2
(45) Date of Patent: Aug. 10, 2021

(54) EXERCISE DEVICE

(71) Applicant: Robert Yanez, Corpus Christi, TX (US)

(72) Inventor: Robert Yanez, Corpus Christi, TX (US)

( * ) Notice: Subject to any disclaimer, the term of this patent is extended or adjusted under 35 U.S.C. 154(b) by 113 days.

(21) Appl. No.: 16/690,679

(22) Filed: Nov. 21, 2019

(65) Prior Publication Data

US 2020/0171343 A1 Jun. 4, 2020

Related U.S. Application Data

(60) Provisional application No. 62/773,330, filed on Nov. 30, 2018.

(51) Int. Cl.
| | | |
|---|---|---|
| *A63B 21/00* | (2006.01) | |
| *A63B 23/04* | (2006.01) | |
| *A63B 21/16* | (2006.01) | |
| *A61F 5/37* | (2006.01) | |

(52) U.S. Cl.
CPC ...... *A63B 21/4011* (2015.10); *A63B 21/1627* (2013.01); *A63B 23/0405* (2013.01); *A61F 5/3761* (2013.01); *A63B 2023/0411* (2013.01); *A63B 2209/14* (2013.01)

(58) Field of Classification Search
CPC ............ A63B 21/4011; A63B 23/0405; A63B 21/1627; A63B 2209/14; A63B 2023/0411; A63B 21/4013; A63B 2225/09; A63B 2209/10; A63B 2071/0063; A63B 2210/50; A63B 71/0054; A63B 2208/0223; A61F 5/3761
See application file for complete search history.

(56) References Cited

U.S. PATENT DOCUMENTS

| | | | | |
|---|---|---|---|---|
| 2,836,335 A | * | 5/1958 | Schuman ............... | A63B 27/02 182/134 |
| 4,274,628 A | * | 6/1981 | Hoagland .......... | A63B 21/0724 482/106 |
| 4,335,875 A | * | 6/1982 | Elkin ................. | A63B 69/0059 482/131 |
| 4,337,938 A | * | 7/1982 | Rodriguez ......... | A63B 69/0059 224/258 |
| 4,529,191 A | * | 7/1985 | Miller ..................... | A63B 1/00 211/123 |

(Continued)

*Primary Examiner* — Garrett K Atkinson
(74) *Attorney, Agent, or Firm* — Boudwin Intellectual Property; Daniel Boudwin

(57) ABSTRACT

An exercise device. The exercise device includes an elongated member with a pair of grooves disposed at opposing ends. A pair of tension screws are utilized to slidably secure a pair of clamps to opposing ends of the elongated member. The pair of clamps slidably adjust along the length of the elongated member by traveling along the grooves. The clamps secure the elongated member to an opening, such as a door frame. The elongated member further includes a pair of recessed portions. The recessed portions are configured to curve around a soleus portion of a user's legs. A pair of straps affixed to opposing ends of each recessed portion removably secure about a front of the user's legs. In one embodiment, the elongated member is hingedly divided into two parts, wherein each part includes a clamp slidably secured thereto and a recessed portion, thereby providing a storage configuration.

18 Claims, 3 Drawing Sheets

(56) References Cited

U.S. PATENT DOCUMENTS

| | | | | |
|---|---|---|---|---|
| 4,629,179 A * | 12/1986 | Bizilia | A63B 23/0211 | 482/140 |
| 4,676,502 A * | 6/1987 | Mahr | A63B 21/065 | 482/105 |
| 4,770,414 A * | 9/1988 | Fredrickson | A63B 23/0211 | 482/148 |
| 4,809,971 A * | 3/1989 | Goldish | A63B 21/1654 | 482/140 |
| 4,863,158 A * | 9/1989 | Tassone | A63B 21/0004 | 482/140 |
| 5,085,437 A * | 2/1992 | Leitao | A63B 69/0059 | 473/212 |
| 5,176,602 A * | 1/1993 | Roberts | A63B 7/02 | 482/129 |
| 5,254,063 A * | 10/1993 | House, Jr. | A63B 21/0728 | 403/104 |
| 5,295,949 A * | 3/1994 | Hathaway | A61F 5/055 | 482/10 |
| 5,556,369 A * | 9/1996 | Roberts | A63B 17/00 | 482/131 |
| 5,634,873 A * | 6/1997 | Carlstrom | A63B 23/03575 | 482/95 |
| 5,637,067 A * | 6/1997 | Ausmus | A63B 21/0004 | 482/140 |
| 5,871,422 A | 2/1999 | Elbogen | | |
| 5,871,424 A * | 2/1999 | Conner | A63B 21/0552 | 482/129 |
| 5,957,818 A * | 9/1999 | Betournay | A63B 21/065 | 482/105 |
| 6,015,371 A * | 1/2000 | Davitt | A63B 21/0552 | 428/121 |
| 6,152,857 A * | 11/2000 | Gonzalez-Leal | A63B 21/0552 | 482/10 |
| D438,577 S * | 3/2001 | Phillips | D21/662 | |
| 6,267,711 B1 * | 7/2001 | Hinds | A63B 1/00 | 482/121 |
| 6,648,804 B2 * | 11/2003 | Chen | A63B 21/0004 | 482/125 |
| 6,764,433 B1 * | 7/2004 | Sims | A63B 21/0552 | 482/139 |
| 6,908,418 B2 * | 6/2005 | Saure | A63B 21/0552 | 482/121 |
| 7,044,896 B2 * | 5/2006 | Hetrick | A63B 21/00043 | 482/95 |
| D588,703 S * | 3/2009 | Boleratz | D24/190 | |
| 7,578,775 B2 * | 8/2009 | Terry | A63B 21/0004 | 482/121 |
| 7,591,772 B2 * | 9/2009 | Shillington | A63B 21/0728 | 482/106 |
| 7,601,100 B1 * | 10/2009 | Hinds | A63B 23/12 | 482/131 |
| 7,621,847 B2 * | 11/2009 | Lamle | A63B 21/00181 | 482/39 |
| 7,621,856 B1 * | 11/2009 | Keith | A01K 27/004 | 119/796 |
| 7,678,033 B2 | 3/2010 | Tyree | | |
| 7,811,202 B2 * | 10/2010 | Planke | A63B 7/02 | 482/7 |
| 7,819,784 B1 * | 10/2010 | Caswell | A63B 21/1627 | 482/95 |
| 7,865,987 B2 * | 1/2011 | Deetsch | A47C 16/00 | 5/640 |
| 7,976,445 B2 | 7/2011 | Lalaoua | | |
| 8,088,050 B2 * | 1/2012 | Aucamp | A63B 23/03533 | 482/131 |
| 8,348,814 B1 * | 1/2013 | Hinds | A63B 23/1218 | 482/82 |
| 8,840,528 B2 * | 9/2014 | Zylstra | A63B 23/025 | 482/10 |
| 8,944,976 B2 * | 2/2015 | Crowell | A63B 21/068 | 482/125 |
| 9,022,908 B2 * | 5/2015 | Crowell | A63B 23/03541 | 482/121 |
| 9,517,374 B2 * | 12/2016 | Alexandrov | A63B 7/02 | |
| 9,555,280 B2 * | 1/2017 | Kaye | A63B 23/1218 | |
| 9,597,541 B2 * | 3/2017 | Hinds | A63B 21/16 | |
| 9,682,267 B2 * | 6/2017 | Kaye | A63B 23/03541 | |
| 9,962,575 B2 * | 5/2018 | Askins | A63B 21/026 | |
| 10,149,998 B2 * | 12/2018 | Wu | A63B 23/0405 | |
| 10,252,099 B2 * | 4/2019 | Karpachevskyy | A63B 21/068 | |
| 10,695,601 B2 * | 6/2020 | Souffrain | A63B 21/068 | |
| 2002/0198081 A1 * | 12/2002 | Chen | A63B 21/00043 | 482/23 |
| 2003/0125170 A1 * | 7/2003 | Vernon | A63B 21/4017 | 482/124 |
| 2003/0158024 A1 * | 8/2003 | Saure | A63B 21/1645 | 482/126 |
| 2004/0097353 A1 | 5/2004 | Mencis et al. | | |
| 2006/0052223 A1 * | 3/2006 | Terry | A63B 21/0004 | 482/126 |
| 2006/0252612 A1 * | 11/2006 | Melcer | A63B 23/0405 | 482/94 |
| 2006/0252615 A1 * | 11/2006 | Melcer | A63B 23/0405 | 482/139 |
| 2007/0161469 A1 * | 7/2007 | Lamle | A63B 23/03533 | 482/94 |
| 2008/0200316 A1 * | 8/2008 | Shillington | A63B 21/0728 | 482/106 |
| 2009/0105053 A1 * | 4/2009 | Hetrick | A63B 21/1663 | 482/133 |
| 2009/0275449 A1 * | 11/2009 | Terry | A63B 23/03525 | 482/139 |
| 2010/0016132 A1 * | 1/2010 | Flynn | A63B 21/4015 | 482/122 |
| 2010/0285938 A1 * | 11/2010 | Latronica | A63B 21/16 | 482/124 |
| 2012/0074083 A1 * | 3/2012 | Geils | A63B 71/0045 | 211/85.7 |
| 2013/0288861 A1 * | 10/2013 | Cole | A63B 23/1263 | 482/102 |
| 2014/0221176 A1 * | 8/2014 | Zylstra | A63B 23/025 | 482/124 |
| 2016/0023051 A1 * | 1/2016 | Lauener | A63B 7/00 | 482/143 |
| 2016/0303419 A1 * | 10/2016 | Karpachevskyy | A63B 21/1636 | |
| 2017/0050076 A1 | 2/2017 | Beals | | |
| 2018/0250546 A1 * | 9/2018 | Wu | A63B 21/4033 | |
| 2020/0384306 A1 * | 12/2020 | Carter | A63B 21/0726 | |

* cited by examiner

EXERCISE DEVICE

CROSS REFERENCE TO RELATED APPLICATIONS

This application claims the benefit of U.S. Provisional Application No. 62/773,330 filed on Nov. 30, 2018. The above identified patent application is herein incorporated by reference in its entirety to provide continuity of disclosure.

BACKGROUND OF THE INVENTION

The present invention relates to exercise equipment. More particularly, the present invention provides a portable exercise device that is removably secured to a door frame, which aids individuals in keeping and maintaining proper form while performing exercises such as squats.

Many people exercise to improve the quality of their life and their health. However, exercise can be a difficult task for beginners. People who are not properly trained and coached may lack the proper form when performing exercises. Such people risk major discomfort, and in some instances, severe injuries resulting from such improper form. Additionally, improper form can lead to muscle imbalances, which can further lead to injury. Beginner exercise enthusiasts may get discouraged from going to a public gym and seeing others complete exercises with little to no perceived effort.

Devices have been disclosed in the known art that relate to exercise equipment. These include devices that have been patented and disclosed in patent application publications. However, the devices in the known art have several drawbacks. Some devices only focus on exercises involving the upper body, and do not provide stability and support for lower-body exercise. Some devices operate through variable resistance cables and do not provide a stable structure. Other devices provide support for lower-body exercises such as squats through a system of supports and frames that engage various aspects of the entire body, thereby minimizing the user's freedom of movement and ability to adapt the exercise device to a wide variety of exercises.

The present invention substantially diverges in design elements from the known art and consequently it is clear that there is a need in the art for an improvement to existing exercise devices. In this regard the present invention substantially fulfills these needs.

SUMMARY OF THE INVENTION

In view of the foregoing disadvantages inherent in the known types of exercise equipment now present in the prior art, the present invention provides an exercise device wherein the same can be utilized for providing stability and support for the user when engaging in various lower-body exercises. The present exercise device comprises an elongated member with a pair of grooves disposed at opposing ends. A pair of tension screws are utilized to slidably secure a pair of clamps to opposing ends of the elongated member. The pair of clamps slidably adjust along the length of the elongated member by traveling along the grooves. The clamps are utilized to secure the elongated member to an opening, such as a door frame. The elongated member further includes a pair of recessed portions. The recessed portions curve around a soleus portion of a user's legs to provide support. A pair of straps affixed to opposing ends of each recessed portion removably secure about a front of the user's legs. In one embodiment, the elongated member is hingedly divided into two parts, wherein each part includes a clamp slidably secured thereto and a recessed portion, thereby providing a storage configuration.

Other objects, features and advantages of the present invention will become apparent from the following detailed description taken in conjunction with the accompanying drawings.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
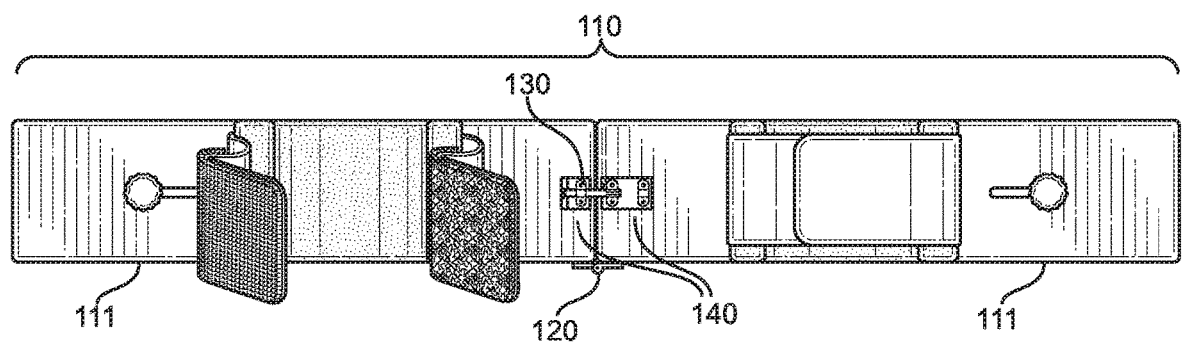
FIG. 1 shows a front view of an embodiment of the exercise device.

Reference is made herein to the attached drawings. Like reference numerals are used throughout the drawings to depict like or similar elements of the exercise device. For the purposes of presenting a brief and clear description of the present invention, a preferred embodiment will be discussed as used for the exercise device. The figures are intended for representative purposes only and should not be considered to be limiting in any respect.

Referring now to FIG. 1, there is shown a front view of an embodiment of the exercise device. The exercise device comprises an elongated member 110. The elongated member 110 is sized to stretch across a width of a doorway and is configured to secure to a doorway opening. In the shown embodiment, the elongated member 110 is divided into a pair of lateral members 111 which are hingedly 120 connected. In such an embodiment, the pair of lateral members 111 are able to be folded in against each other, and in such a manner the exercise device can hingedly 120 close into a storage configuration. In a further embodiment, a locking bolt 130 is slidably disposed across medial surfaces 140 of the pair of lateral members 111. In such an embodiment, the locking bolt 130 is able to secure the lateral members 111 side-by-side in an open configuration. In the embodiment in which a pair of lateral members 111 are utilized, the side-by-side configuration provides a length needed to span the width of the doorway. In such an embodiment, each lateral member 111 is a shorter length than the width of the doorway.

Figure 2:
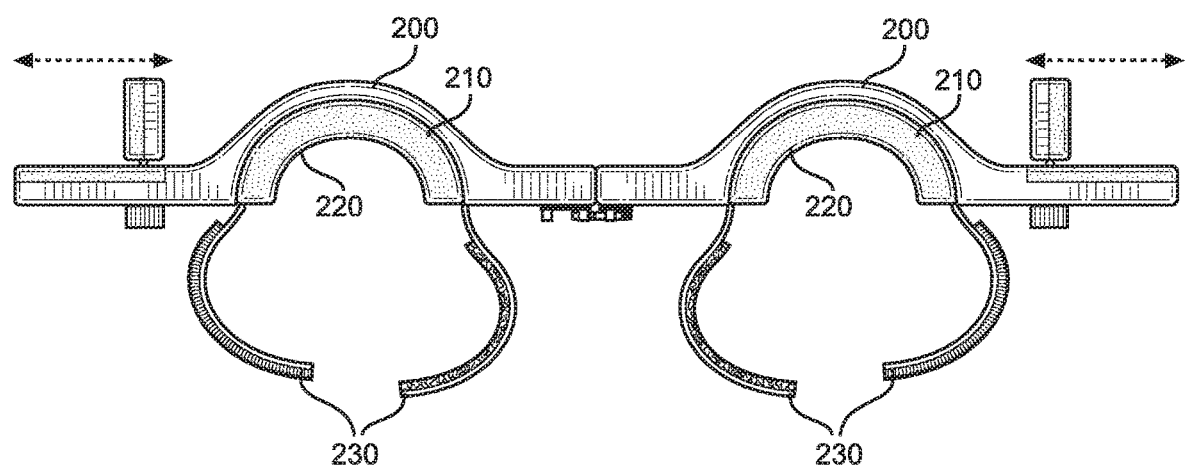
FIG. 2 shows a top-down view of an embodiment of the exercise device.

Referring now to FIG. 2, there is shown a top-down view of an embodiment of the exercise device. The elongated member further comprises a pair of recessed portions 200. The recessed portions 200 are configured to curve around a soleus portion of a user's legs. In one embodiment, the recessed portion 200 is configured to also curve around a user's ankle. The recessed portions 200 are disposed and spaced apart on the elongated member such that a user is able to position each of their legs into one of the recessed portions 200 resulting in the user's feet being placed a width apart from each other. In one embodiment, the recessed portions 200 are spaced such that a user's feet are width apart corresponding to a width of the user's shoulders. Such a spacing allows a user to maintain a stable and proper position and form while performing exercises such as squats.

A padded material 220 is disposed on a front surface 210 of the recessed portions 200. Such a padded material 220 provides added comfort to the user and prevents the user from rubbing the backs of their legs against the elongated member. The padded material 220 also provides a custom fit between the recessed portions 200 and the backs of the user's legs, thereby providing a more secure and stable fit of the elongated member to the user. Such a padded material 220 is able to conform to the unique shape of the user's individual legs.

A pair of straps 230 are affixed to opposing ends of each of the recessed portions 200. The straps 230 are utilized to secure the user's legs in the recessed portions 200. The straps 230 are configured to be removably securable about a front portion of the user's legs. In one embodiment, the user secures their legs in the recessed portions 200 with their legs spaced a shoulder's width apart and thereby maintains a stable and secure base from which the user is able to perform their exercises utilizing the proper stance and form. In one embodiment, the straps 230 are selectively adjustable to provide the user with a custom fit around each leg. In one embodiment, the straps 230 comprise a break-away material such that where force is applied to the material, such as where a user falls, the material will separate and the straps 230 will not cause injury to the user. The break-away material also ensures that the user is not injured in a fall by being held in place by the straps 230. In a further embodiment, the break-away material of the straps 230 comprise complimentary hook and loop fasteners. In another embodiment, the straps 230 comprise a plurality of apertures and a complementary receiving buckle.

Figure 3:
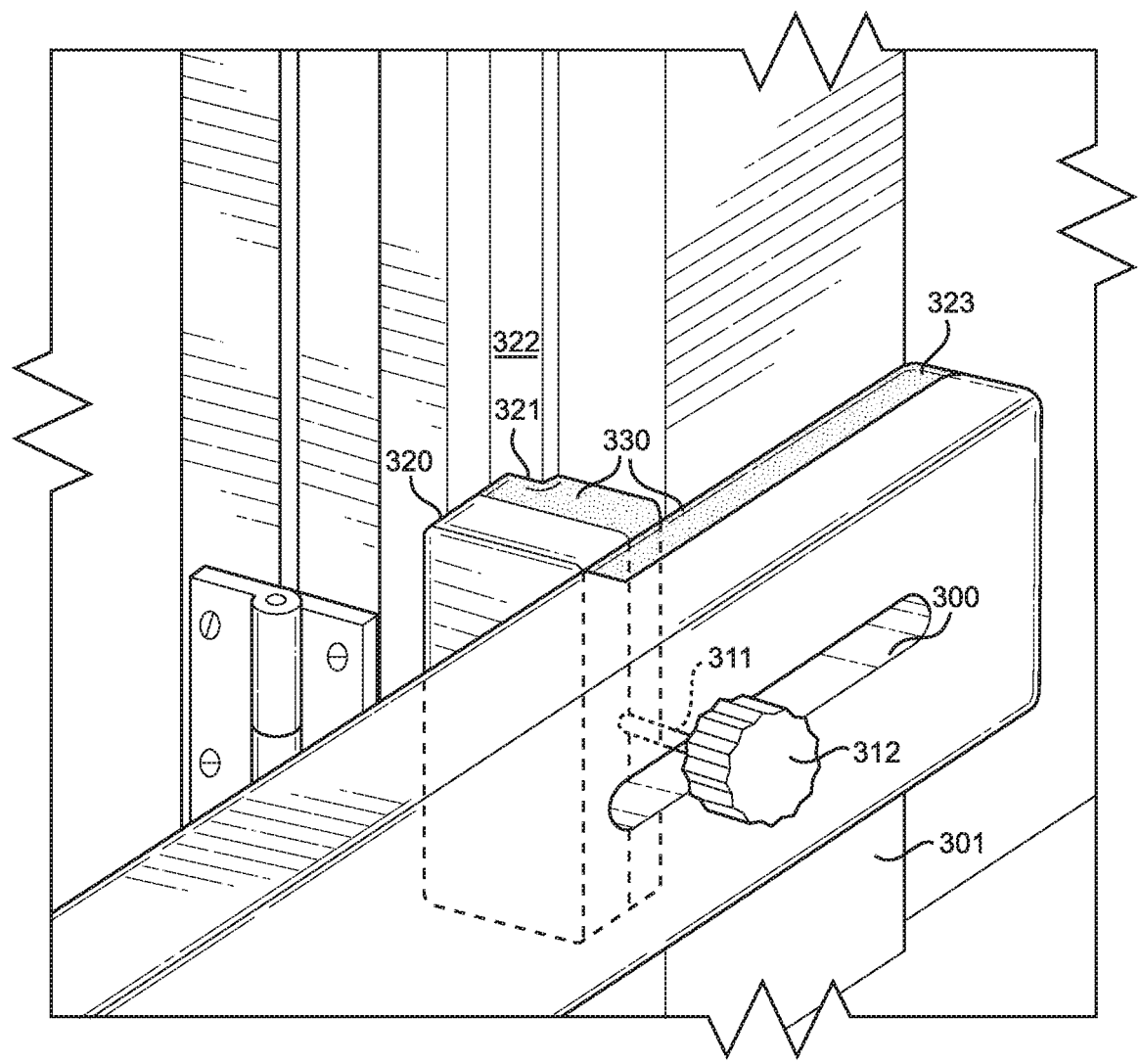
FIG. 3 shows a perspective view of an embodiment of the exercise device, with a focus on the clamps.

Referring now to FIG. 3, there is shown a perspective view of an embodiment of the exercise device, with a focus on the clamps. A pair of grooves 300 are disposed at opposing ends of the elongated member. In the shown embodiment, the grooves 300 traverse a horizontal portion of each end of the elongated member. The grooves 300 are sized to receive a shaft 311 of a tension screw. In one embodiment, a pair of tension screws are slidably received by the grooves 300 of the elongated member at opposing ends thereof. A head 312 of the tension screw is sized to be larger than a width of the groove, such that the shaft 311 of the tension screw is received within the groove and the head 312 of the tension screw compresses against the elongated member. The head 312 of the tension screw is configured to be rotated such that the tension screw can be loosened, thereby enabling a user to slide the tension screw along the groove 300, or tightened, thereby locking the tension screw at a given position in the groove 300 via compression of the head 312 against the elongated member. In one embodiment, the shaft 311 of the tension screw is threaded and received by a complementary threading in a pair of clamps 320.

A distal end of the shaft 311 of the tension screw is secured in a single clamp 320 of a pair of clamps 320. The pair of clamps 320 slidably adjust along the opposing lengths of the elongated member by traveling along a length of the grooves 300. A back surface 323 of the elongated member is configured to rest against a horizontal face 301 of a doorway, while a mating surface 321 of the clamps 320 is configured to rest along a lateral face 322 of the doorway. In such a manner, the user can adjust the spacing between the pair of clamps 320 to firmly secure the elongated member to a doorway. In one embodiment, the clamps 320 are configured to removably secure the elongated member to a doorway via friction. In a further embodiment, the clamps 320 are configured to removably secure the elongated member to a frame of a door via friction.

In various embodiments, the back surface 323 of the elongated member and the mating surface 321 of the clamp 320 further comprise a compression material 330. Such a compression material 330 is configured to aid in securing the back surface 323 of the elongated member, as well as the mating surface 321 of the clamp 320, to the door 302 via friction. In one embodiment, the compression material 330 comprises rubber. In another embodiment, the compression material 330 comprises plastic.

Figure 4:
FIG. 4 shows a perspective view of an embodiment of the exercise device in use.

Referring now to FIG. 4, there is shown a perspective view of an embodiment of the exercise device in use. In use, a user extends the elongated member 110 across an open doorway 400. In one embodiment, the user loosens the tension screws and adjusts the placement of the clamps 320 such that the mating surface firmly abuts the sides of the doorway 400 or door frame 401. The user tightens the tension screws, and in such a manner, firmly secures the elongated member 110 within the doorway 400. The user then positions themselves such that their ankles and the soleus portions of their legs are aligned with and are in contact with the recessed portions 200 of the elongated member. The user then adjusts the length and tightness of the pair of straps 230 to secure their legs into the elongated member. In such a manner, the exercise device aids a user in maintaining stability while performing lower-body exercises such as squats.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:
1. An exercise device, comprising:
   an elongated member;
   a pair of grooves disposed at opposing ends of the elongated member;
   a pair of tension screws, wherein a shaft of a single screw is slidably received within one of the opposing grooves in the elongated member;
   a head of the tension screws dimensioned to be larger than a width of the groove;
   a distal end of each tension screw secured into a single clamp of a pair of clamps;
   the pair of clamps slidably adjustable along the opposing lengths of the elongated member by traveling along a length of the grooves;

the elongated member further comprising a pair of recessed portions;

a pair of straps affixed to opposing ends of each recessed portion;

the pair of straps removably securable about a front of the user's legs.

2. The exercise device of claim 1, wherein the elongated member further comprises a compression material on a back surface.

3. The exercise device of claim 1, wherein the clamp further comprises a compression material on a lateral surface.

4. The exercise device of claim 1, wherein the recessed portion further comprises a padded material on a front surface thereof.

5. The exercise device of claim 4, wherein the padded material comprises memory foam.

6. The exercise device of claim 1, wherein the pair of straps further comprise fasteners.

7. The exercise device of claim 6, wherein the fasteners comprise hook and loop material.

8. The exercise device of claim 1, wherein the recessed portions comprise an arcuate configuration.

9. The exercise device of claim 1, wherein the recessed portions are shaped to curve around a soleus portion of a user's legs.

10. An exercise device, comprising:

an elongated member, further comprised of a pair of lateral members;

the pair of lateral members, hingedly connected;

a locking bolt slidably disposed across a medial surface of the pair of elongated members;

a pair of grooves disposed at opposing ends of the elongated member;

a pair of tension screws, wherein a shaft of a single screw is threaded through one of the opposing grooves in the elongated member;

a head of the tension screw sized larger than a width of the groove;

a distal end of each tension screw secured into a single clamp of a pair of clamps;

the pair of clamps slidably adjustable along the opposing lengths of the elongated member by traveling along a length of the grooves;

the elongated member further comprising a pair of recessed portions;

the recessed portions curve around a soleus portion of a user's legs;

a pair of straps affixed to opposing ends of each recessed portion;

the pair of straps removably securable about a front of the user's legs.

11. The exercise device of claim 10, wherein the elongated member further comprises a compression material on a back surface.

12. The exercise device of claim 10, wherein the clamp further comprises a compression material on a lateral surface.

13. The exercise device of claim 10, wherein the recessed portion further comprises a padded material on a front surface thereof.

14. The exercise device of claim 13, wherein the padded material comprises memory foam.

15. The exercise device of claim 10, wherein the pair of straps further comprise fasteners.

16. The exercise device of claim 15, wherein the fasteners comprise hook and loop material.

17. The exercise device of claim 10, wherein the recessed portions comprise an arcuate configuration.

18. The exercise device of claim 10, wherein the recessed portions are shaped to curve around a soleus portion of a user's legs.

* * * * *